US009283146B2

(12) United States Patent
Aguerre et al.

(10) Patent No.: US 9,283,146 B2
(45) Date of Patent: Mar. 15, 2016

(54) MACHINE AND METHOD FOR THE AUTOMATIC PREPARATION OF INTRAVENOUS MEDICATION

(75) Inventors: Jean-Philippe Aguerre, Itxassou (FR); Borja Lizari Illarramendi, Vitoria-Gastelz (ES); Susana Soto Iglesias, Gipuzkoa (ES); Naiara Telleria Garay, Gipuzkoa (ES); Gerardo Cajaraville Ordonana, Gipuzkoa (ES); Maria Jose Tames Alonso, Gipuzkoa (ES)

(73) Assignee: KIRO ROBOTICS, S.L., Gipuzkoa (ES)

( * ) Notice: Subject to any disclaimer, the term of this patent is extended or adjusted under 35 U.S.C. 154(b) by 160 days.

(21) Appl. No.: 13/877,589

(22) PCT Filed: Jun. 15, 2012

(86) PCT No.: PCT/IB2012/001180
§ 371 (c)(1),
(2), (4) Date: Apr. 3, 2013

(87) PCT Pub. No.: WO2012/172418
PCT Pub. Date: Dec. 20, 2012

(65) Prior Publication Data
US 2014/0150379 A1    Jun. 5, 2014

(30) Foreign Application Priority Data

Jun. 17, 2011  (EP) .................................... 11382202
Jun. 17, 2011  (EP) .................................... 11382203

(51) Int. Cl.
*A61J 3/00*    (2006.01)
*B65B 3/00*    (2006.01)
(Continued)

(52) U.S. Cl.
CPC . *A61J 3/002* (2013.01); *B08B 9/08* (2013.01); *B08B 15/023* (2013.01); *B65B 3/003* (2013.01);
(Continued)

(58) Field of Classification Search
CPC ....... B65B 3/003; B65B 3/04; A61M 5/1782; A61J 3/002; B08B 9/08; B08B 15/023; B01F 13/1055; B01L 3/0241; B01L 2200/023; B01L 2300/0838
USPC ................... 141/319, 329, 330, 331; 700/245
See application file for complete search history.

(56) References Cited

U.S. PATENT DOCUMENTS

| 2,702,505 A | 2/1955 | Nelson |
| 5,341,854 A * | 8/1994 | Zezulka ..................... A61J 1/20 141/1 |

(Continued)

FOREIGN PATENT DOCUMENTS

| EP | 1759776 | 3/2007 |
| WO | 2006124211 | 11/2006 |

(Continued)

OTHER PUBLICATIONS

Singapore Search Report and Written Opinion mailed Jan. 7, 2015 for Singapore Application No. 2013089693.

*Primary Examiner* — Timothy L Maust
(74) *Attorney, Agent, or Firm* — RatnerPrestia

(57) ABSTRACT

Machine and method for the automatic preparation of medication, comprising:—a starting products area comprising at least one receptacle with bane products; a transfer tools area further comprising at least one transfer tool; a prepared products area comprising at least one container; and one robot with holding means for transporting the receptacle, the transfer tool and/or the container; wherein the robot, the starting products area, the transfer tools area, and the prepared products area are disposed in the same cabinet or chamber of the machine, so that the robot is adapted to transport the receptacle, the transfer tool and/or the container between the areas in the chamber. The machine further comprising a holding device between the receptacle, the transfer tool or the container and the robot's holding means, said holding device comprising elastic means for fixation to different sizes/forms of receptacles, transfer tools or containers.

19 Claims, 9 Drawing Sheets

(51) Int. Cl.
  *B08B 15/02* (2006.01)
  *B08B 9/08* (2006.01)
  *B01F 13/10* (2006.01)
  *B01L 3/02* (2006.01)
  *B01L 9/06* (2006.01)

(52) U.S. Cl.
  CPC ............ *B01F 13/1055* (2013.01); *B01L 3/0241* (2013.01); *B01L 9/06* (2013.01); *B01L 2200/023* (2013.01); *B01L 2300/0838* (2013.01)

(56) References Cited

U.S. PATENT DOCUMENTS

| | | | | |
|---|---|---|---|---|
| 5,431,201 A | * | 7/1995 | Torchia | A61J 1/20 141/100 |
| 5,479,969 A | * | 1/1996 | Hardie | B65B 3/003 141/103 |
| 7,289,879 B2 | * | 10/2007 | William | G07F 11/165 221/10 |
| 7,343,943 B2 | * | 3/2008 | Khan | B65B 3/003 141/2 |
| 7,610,115 B2 | * | 10/2009 | Rob | A61J 1/20 318/568.11 |
| 8,386,070 B2 | * | 2/2013 | Eliuk | A61J 1/20 141/1 |
| 8,820,365 B2 | * | 9/2014 | Aguerre | B65B 3/003 141/192 |
| 8,857,476 B2 | * | 10/2014 | Koike | A61J 3/002 141/114 |
| 2008/0169044 A1 | | 7/2008 | Osborne et al. | |
| 2008/0199353 A1 | | 8/2008 | Mlodzinski et al. | |
| 2009/0223592 A1 | | 9/2009 | Procyshyn et al. | |
| 2010/0268167 A1 | | 10/2010 | Mattioli | |

FOREIGN PATENT DOCUMENTS

| WO | WO 2008047390 | 4/2008 |
|---|---|---|
| WO | WO 2009147252 | 12/2009 |
| WO | WO 2011007341 | 1/2011 |

* cited by examiner

MACHINE AND METHOD FOR THE AUTOMATIC PREPARATION OF INTRAVENOUS MEDICATION

This application is a 371 application of PCT/IB202/001180, filed Jun. 15, 2012, which claims priority to EP Application No. 11382202.7, filed Jun. 17, 2011 and EP Application 11382203.5, filed Jun. 17, 2011, each of which is incorporated by reference in its entirety herein.

DESCRIPTION

This invention relates to machines for the automatic preparation of intravenous medication.

Machines for the automatic preparation of intravenous medication are known from prior art. The medication is the result of the mixture of specific amounts of different base products, and in may cases, once said medication has been prepared, it is packaged in containers adapted to house it. The base products are stored in vials and a preset amount is removed from them, sufficient to generate the required intravenous medication.

Medications are prepared manually in many hospitals, although an increasing number of hospitals now have a machine to prepare medications. The vials or receptacles housing the necessary base products are disposed in the machine, and said machine handles said vials in order to create a mixture of the base products they house, in the required quantities for each of them and in the required order.

One of these machines is disclosed in document WO 2009147252 A1. Said machine comprises different work areas that are separate to each other, such as a storage are where the receptacles or vials are disposed, and a preparation area where the final medication, based on the base products present in said vials, is prepared.

Furthermore, document US2008/0199353 A1 discloses an automatic pharmacy admixture system comprising a robotic arm and several actuation stations (for example, a decapper station, a syringe manipulator station, etc.) wherein the robotic arm acts as a conveying device between stations for different types of receptacles.

Using the same robotic arm to act on different type of receptacles requires that the robotic arm comprises a clamp that can act on a vial with vial diameter from approximately 15 to 55 millimeters while maintaining the accuracy. This kind of clamping requires complex programming and a program instruction for each type of receptacle further to the hazard that represents acting directly on a breakable material as in the case for glass vials. Furthermore, it is extremely difficult and expensive to find the adequate clamps for this kind of work.

Therefore, it is already too complex to convey different kinds of receptacles for a device as disclosed in US2008/0199353 A1 for intending to, in addition, perform actions such as moving the piston of a syringe or agitating a vial.

It is an object of the invention to provide a machine for the automatic preparation of intravenous medication, as described in the claims.

According to a first aspect of the machine of the present invention, the machine comprises a starting products area where the base products from which the required medication is generated are disposed, a transfer tools area where at least one syringe that is used to prepare the required mediation is disposed, a prepared products area to house the prepared medication, and at least one robot to communicate the different areas with each other.

The robot, the starting products area, the transfer tools area, and the prepared products area are disposed in the same cabinet or chamber of the machine, so that said robot is adapted to communicate said areas with each other in said chamber, transporting the receptacles, the syringe and/or the container from one area to another to prepare the required medication. Furthermore, the robot according to the present invention is capable of actuating on a receptacle by the addition of a holding device adapted to provide a better grip to a receptacle.

As a result, as all the operations for the preparation of the intravenous medication can be carried out in the same cabinet or chamber, the different areas are not isolated from each other and, for example, in the event of the machine breaking down a user can access said chamber and carry out the preparation of said medication manually, being able to make use of the space occupied by the machine for the dame medication preparation function even when said machine is not working. In addition, as it does not comprise storage members and/or carrousels where different receptacles and containers are stored, for example, there is no need to use additional movement tools to position the required receptacles and containers in a final position adapted for the preparation of the intravenous medication in progress as, in the machine of the invention, they are already disposed in said final position.

Surprisingly, a device according to the present invention diminishes the need and quantity of different stations for each of the actions that have to be performed on the receptacles. For example, the holding device can provide a better grip to a vial allowing the robot to transport and agitate the vial, therefore eliminating the agitation station from the prior art vials. Another action on vials could be the reconstitution of a lyophilized medication, a robot with a holding device according to the present invention could press the vial against a needle, a spike or any means for perforating the elastomeric part of a vial in order to inject dissolutive fluid into the vial, therefore replacing the fixed reconstitution station for a peristaltic pump that performs a more accurate, precise and faster dosification of the reconstitution solvent. In addition, such a holding device works as an standardization device given that it may hold receptacles of different sizes/forms while maintaining a common exterior shape so the robot does not need to detect the size/form of every vial prior to its manipulation. Furthermore, such a device may provide a "centering" of the vial, this is, that every vial's elastomeric portion (the portion meant to be penetrated by a needle) have the same position in respect to the holding device or, at least, maintain one common coordinate.

Also, the holding device may be a device adapted for transfer tools wherein said holding device comprises gripping means and a plunger actuator so that the actuation of the transfer tool can occur anywhere in the chamber, only limited by the arm's capability to get to the point where the actuation is required.

According to s second aspect of the present invention, the machine can comprise at least two robotic arms, being one of the said robotic arms dedicated for the transport and/or actuation of receptacles and another one of the said robotic arms dedicated for the transport and/or actuation of transfer tools. Such an invention may provide faster procedures given that, for example, while one of the arms performs actions on a vial the other can measure, remove caps of syringes, etc. Surprisingly, the use of an arm for each of the receptacles provides more safety, given that more adequate holding means can be provided for each of the robots (e.g. different sized or shapes of the clamps).

Also, the present invention allows a better cleaning of a machine given that the number of fixed stations is lowered, and robotic arms can be moved around the machine in order to let water through critical spots of the machine, therefore allowing a better cleaning in its most important areas.

These and other advantages and characteristics of the invention will be made evident in the light of the drawings and the detailed description thereof.

FIG. 1 shows a preferred embodiment of the machine designed for the preparation of medication from at least one base product, in particular for the preparation of intravenous cytotoxic medicines.

Figure 1:
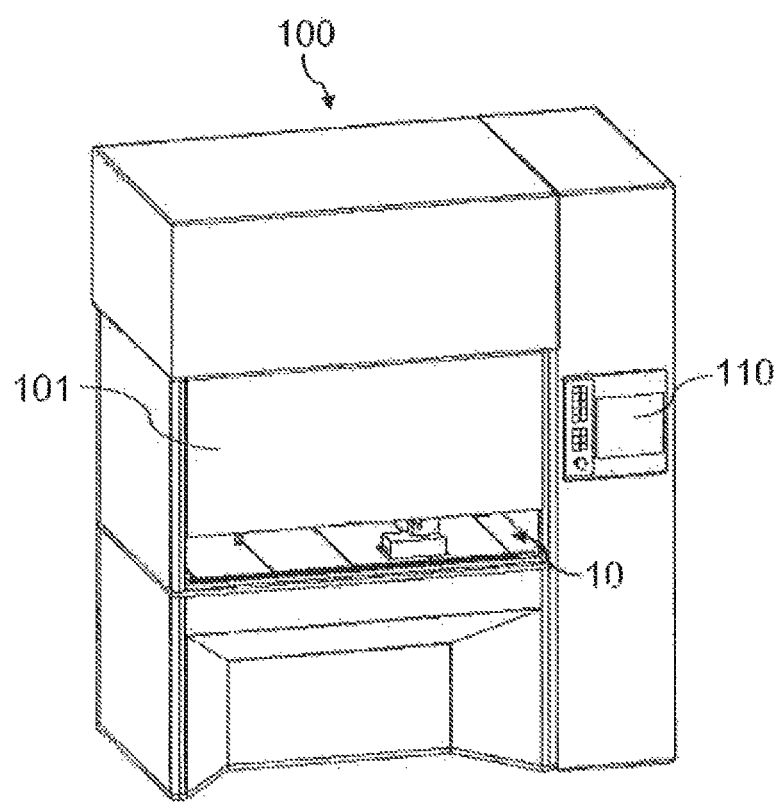
FIG. 1 shows a perspective view of an embodiment of the machine of the invention.
Figure 2:
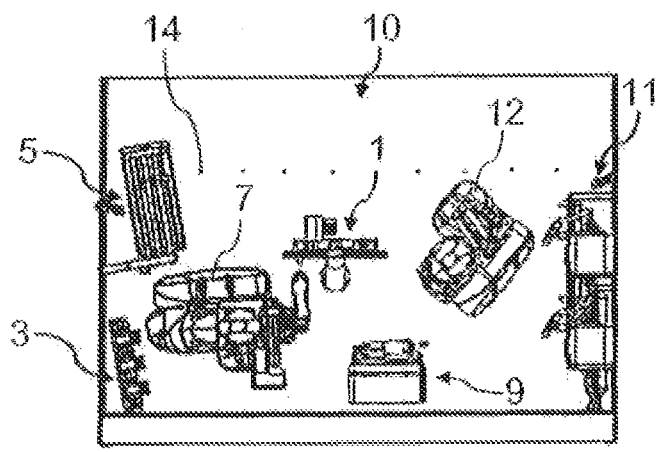
FIG. 2 shows a front view of a chamber or cabinet of the machine of FIG. 1, where the automatic preparation of medication is carried out.
Figure 3:
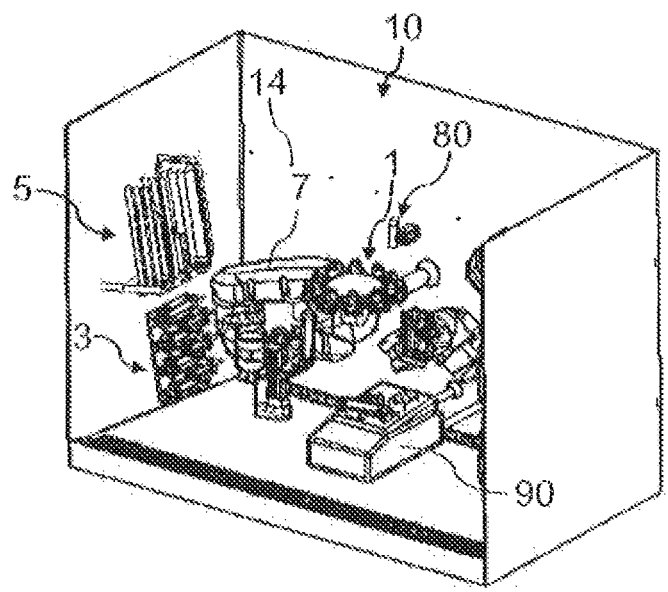
FIG. 3 is a perspective view of the chamber or cabinet of FIG. 2.
Figure 4:
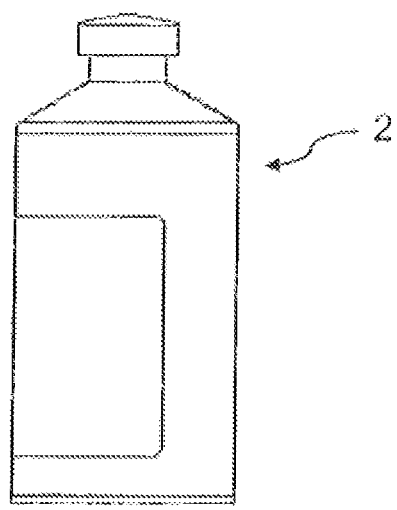
FIG. 4 shows an example of a receptacle among those used in the machine of FIG. 1.
Figure 5:
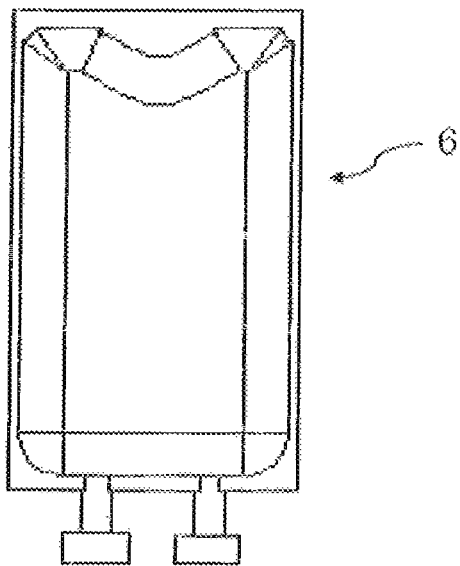
FIG. 5 shows an example of a container among those used in the machine of FIG. 1.

With reference to FIGS. 2 and 3, which correspond with a cabinet or chamber -10- of the preferred embodiment of the machine -100-, said machine -100- comprises a starting products area -1- where base products from which the required medication is generated are disposed manually, which are preferably housed inside receptacles -2- comprising a head, a neck below the head and a body below said neck that preferably correspond with vials such as the one shown by way of example in FIG. 4, each base product in a receptacle -2-, a transfer tools area -3- where as many transfer tools -4- as will be needed during the preparation of the medication are manually disposed, a transfer tool -4- which can be a syringe, a prepared products area -5- where at least one container -6- adapted to house the prepared medication is disposed manually, the container -6- which can be a perfusion bag such as the one shown by way of example in FIG. 5, or either a bottle or an elastomeric infuser, for example, and at least one robot -7- to transport and/or actuate on the receptacles -2-, which can be an articulated arm, the transfer tool -4-, and/or the container -6- to carry out the preparation. The robot -7- and the area -1-, -3- and -5- are disposed in the same cabinet or chamber -10- of the machine -100-, so that the robot -7- is disposed to communicate said area -1-, -3- and -5- with each other in said chamber -10- transporting the receptacles -2-, the transfer tool -4- and/or the container -6- from one area to another to prepare the required medication.

In a preferred embodiment, the robot -7- is adapted to transport a transfer tool -4- from one area to another to prepare the required medication, without transporting the receptacles -2- and the containers -6-, so that the robot -7- carries the transfer tools -4- to the corresponding receptacles -2- and container -6-. Said robot -7- is thus adapted to pick up a transfer tool -4- from the transfer tools area -3- and transport it to the starting products area -1- to cause the total or partial filling of said transfer tool -4- with the necessary or required amount of the base product present in a corresponding receptacle -2-, and to then transport said transfer tool -4- to the prepared products area -5- to cause said transfer tool -4- to empty totally or partially in at least one corresponding container -6-. Although the medication is normally generated with a single base product, in some cases a mixture of different base products is needed to obtain the required medication, cases in which a different transfer tool -4- is used for each base product. Once the contents of a transfer tool -4- have been discharged in a container -6-, the robot -7- deposits said transfer tool -4- in the transfer tools area -1- and picks up a new transfer tool -4- disposed beforehand in said transfer tools area -1- in order to fill it totally or partially with a new base product, the aforementioned process starting again until the required amount of said base product is deposited in the container -6-. The mixture of base products needed to create the required medication is thus generated and deposited or stored in said container -6-.

Figure 6:
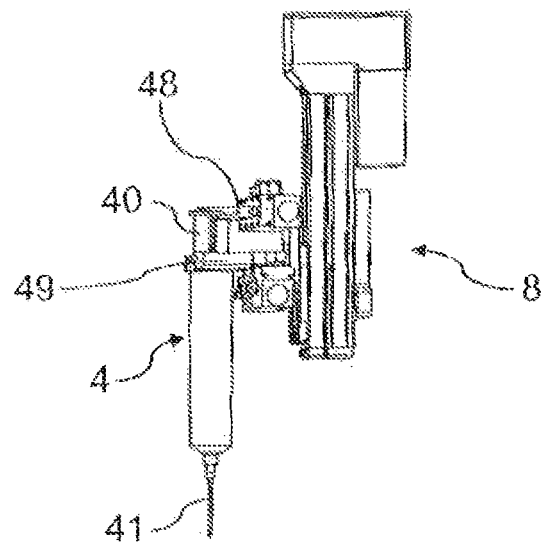
FIG. 6 shows a tool for a robot of the machine of FIG. 1, which is adapted to pick up and handle transfer tools, with a transfer tool.

In the preferred embodiment the machine -100- comprises a tool -8- that is fixed to the robot -7-, shown in FIG. 6, by means of which said robot -7- holds and handles the transfer tools -4-. Said tool -8- comprises clamps -49- or equivalent members controlled by the robot -7- to hold a transfer tool -4-, which can be a syringe, and comprises an actuator -48- to act on a plunger -40- of the syringe and enable the total or partial filling and/or emptying of said syringe, the movement of the plunger -40- being controlled by said actuator -48-, which is controlled by control means such as a microprocessor for example (not shown in the figures), of the machine -100-. The receptacles -2- are disposed in a substantially vertical position with the inlet access disposed in the bottom part, and the robot -7- positions the syringe -4-, by means of the tool -8-, in a substantially vertical position facing the corresponding receptacle -2- in order to fill, totally or partially, said syringe with the corresponding base product. The same thing occurs in order to empty the contents of said syringe in the container -6-. Once the syringe has been positioned in this way, the robot -7- causes a vertical upwards movement of said syringe towards the corresponding receptacle -2- or container -6- until a needle -41- (or an equivalent device/system that may be used as an injection system) of said syringe is introduced into said receptacle -2- or said container -6-, and the actuator -48- then acts on the plunger -40- of the syringe in order to fill the syringe with the required amount of the base product present in the corresponding receptacle -2- or in order to transfer, totally or partially, the contents of said syringe into the corresponding container -6-. Evidently, the plunger -40- moves in an opposite direction when filling and emptying a syringe.

In the preferred embodiment the machine -100- can also comprise, in the chamber -10-, a reconstituting area -11- to reconstitute the receptacles -2- comprising a powdered or lyophilised base product in their interior. Reconstituting should be understood as making a powdered or lyophilised base product soluble in liquid or dissolving it, and in the reconstituting area -11- the machine -100- comprises dosage means (not shown in the figures), which are not detailed as they are not the object of the invention, and which can be conventional, and whose function is to introduce a specific liquid into the receptacle -2- with the base product to be reconstituted. For the reconstitution, the machine -100- can comprise a second robot -12- that is adapted to pick up a receptacle -2- from the starting product area -1- in order to transport it to the reconstituting area -11-, and to transport it again to said starting product area -1- once the contents of the receptacle -2- have been reconstituted, so that a transfer tool -4- can now be filled with the content of said receptacle -2-. Besides, in the preferred embodiment the machine -100- can also comprise a tool not shown in the figures that is disposed in the starting products area -1- for each receptacle -2-, supporting a corresponding receptacle -2-, and the second robot -12- picks up the corresponding tool in order to transport the required receptacle -12-. Although in the preferred embodiment the machine comprises a second robot -12- for the reconstitution, it would also be possible to use the robot -7- to perform said function without the need to include a second robot -12-.

In the preferred embodiment the machine -100- can also comprise a weighing area -9- in the chamber -10- to weigh both the transfer tools -4- and the receptacles -2-, by means of scales -90- or an equivalent member. The corresponding robot -7- or -12- disposes a transfer tool -4- or a receptacle -2- on said scales -90- in order to weigh it.

Figure 7:
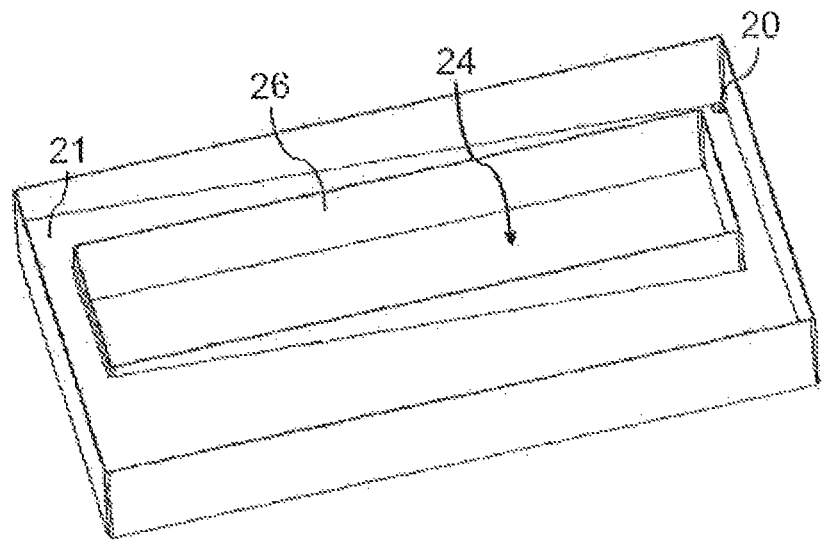
FIG. 7 shows drainage means of the machine of FIG. 1.

The machine -100- can also comprise cleaning means to clean the chamber -10- automatically once the medication has been prepared or after various preparation cycles. Said cleaning means comprise at least one hole -14- through which a sprayed liquid or a fluid in the form of a jet is introduced into one or more certain areas of said chamber -10- or in said chamber -10- in its entirety, which can be water. As a result, the fluid sweeps the surfaces of the chamber -10- and also washes away any dirt or chemicals that can have adhered to the robot -7-, to the second robot -12- if any, and on the different areas -1-, -3-, -5-, -9- and -11-, for example, which are made, at least in the outer part, of a material resistant to the fluid to be used (for example water). Said machine -100- also comprises drainage means, shown in FIG. 7, to drain the chamber -10- of the fluid introduced by the cleaning means. The drainage means comprise at least one drainage hole -20- disposed in the bottom part of the chamber -10- and at least one drainage surface -21- in said bottom part of the chamber -10-, on which at least part of the fluid introduced falls. Said drainage surface -21- comprises a slope that runs downwards to the drainage hole -20- to direct the fluid towards said drainage hole.

The machine -100- can also comprise drying means to dry the walls that delimit the chamber -10- and the elements present in said chamber -10- of the fluid introduced by the cleaning means, said drying means comprising an inlet access (not shown in the figures), in the top part of the chamber -10-, at least one airflow router (not shown in the figures), preferably a fan, on said chamber -10- to force said airflow inside said chamber -10- through the inlet access and until it is removed from said chamber -10- through the bottom part of said chamber -10-, and an outlet access -24- disposed in said bottom part of the chamber -10- through which said airflow is forced out of said chamber -10-. As a result, thanks to the drainage and to the drying the fluid is removed from the chamber -10- completely, resulting in the suitable cleaning of said chamber -10-. The inlet and outlet accesses and the airflow system can also be used during the preparation of the required medication, to ensure that the air in the chamber -10- is purified and insulated from the exterior and also that potentially contaminated air does not escape from the chamber -10- to the exterior (protection of the user and the environment). In said preferred embodiment, the machine -100- also comprises a filter not shown in the figures which is disposed in the outlet access -24- under the preparation area, -10- so that the air that is removed from the chamber -10- passes through said filter toxic or unwanted chemicals not escaping from said chamber -10-. Said filter is surrounded by drainage surfaces -21- of the drainage means, and each one of said drainage surfaces -21- comprises a wall -26- on the side closest to said filter, thereby ensuring that during the preparation or the drainage no liquid reaching said drainage surfaces -21- can dampen the filter. Evidently the filter can be disposed in another position in which it does not need to be surrounded by drainage surfaces -21-, such as against an internal wall of the chamber -10-. Preferably the filter is an HEPA, ULPA, or activated charcoal filter.

The machine -100- can also comprise a user interface -110- to allow a user to programme the medication to be prepared, so that the robot -7- or the robots -7- and -12- act in the manner required to obtain said medication.

A method for the preparation of intravenous medication is explained below. Firstly, the receptacles -2- with the required base products from which the required medication is generated are manually disposed in the starting products area -1-, the transfer tools -4- necessary to prepare said medication are manually disposed in the transfer tools area -3-, and the necessary containers -6- are manually disposed in the prepared products area -5-. For this purpose, the user or users carrying out these operations accesses the chamber -10- by opening in a partial manner to completely a cover -101- of the machine -100- that covers the front of said chamber -10-, so that it is also kept insulated from the exterior.

Once these manual operations have been carried out, a user enters the necessary data or information in the machine -100- through the interface -110-, for example, for the preparation (this step is preferably carried out prior to the pre-preparation), and gives the order for the procedure to start. The necessary information can comprise the necessary information with regard to the base products to be used and to the amounts of each base product to be used, for example, although this information can also be pre-stored in a memory of the machine, for example (entered when carrying out a pre-preparation or even entered before any preparation is carried out), in which case the user only has to indicate which preparation should be carried out.

Once the necessary receptacles -2-, transfer tools -4- and container -6- have been disposed in their corresponding area -1-, -3-, and -5-, the robot -7- carries out a preparation operation in which it picks up a transfer tool -4- from the transfer tools area -3-, transports said transfer tool -4- to the starting products area -1-, causes the transfer tool -4- to be filled partially or completely with a specific amount of a base product present in a corresponding receptacle -2-, transports said transfer tool -4- with said base product to the prepared products area -5-, and empties said transfer tool -4- partially or completely into a corresponding container -6-. The robot -7- carries out as many preparation operations as are necessary to prepare the required amount of medication, using the same transfer tool -4- for each different base product. When all the necessary operations have been completed, when the required medication is deemed to have been prepared, the machine -100- can indicate the end of the preparation with visual and/or sound alarms, for example. Once the required medication has been prepared, a user accesses the chamber -10- to collect the container -6- housing said medication. Similarly, once the robot -7- has used a transfer tool -4- said robot -7- disposes of said transfer tool -4-, depositing it, for example, in a location designed for such a purpose and not shown in the figures.

The robot -7-, in a preferred embodiment of the method, only handles the transfer tools -4- and fills them with a liquid base product. Meanwhile, the control means identify if any receptacle -2- comprises a powdered or lyophilised base product, and if this is the case, a second robot -12- controlled by said control means transports said receptacle -2- from the starting products area -1- to a reconstituting area -11- where said base product is dissolved, changing to a liquid state, and returns it once more to said starting products area -1-. In addition, the second robot -12-, after the corresponding liquid has been introduced into the receptacle -2- in said reconstituting area -11-, shakes said receptacle -2- so that the base product dissolves correctly before transporting it to said starting products area -1- again. The reconstituting operation can be performed at the same time as the preparation operation performed by the robot -7-, while one robot prepares the mixture with base products in a liquid state (the robot -7-), the other robot (second robot -12-) can at the same time be reconstituting a receptacle -2- whose contents are not in a liquid state. This results in a very flexible and speedy preparation method. As stated above, in another embodiment the reconstituting operation can also be carried out by the robot -7-, without the need for the machine -100- to comprise a second robot -12-.

The method can also comprise a weighing phase to determine whether the amount of a base product contained in a syringe is suitable or not.

The method can also comprise a weighing phase for the reconstituted receptacle, in which the second robot -12- transports the reconstituted receptacle -2- to the weighing area -9- to weigh it. It can thus be ascertained if the amount of liquid added to said receptacle for the reconstitution is correct.

To ensure that the base product to be filled in a transfer tool -4- is the correct one, the machine -100- can comprise at least one video system, such as a video camera -80-, for example, and the receptacles -2- can comprise an adhesive label identifying the base product, a computer program of the machine identifies the product and determines whether the product is the correct one and if it needs to be reconstituted. Thus, by reading said label it can be determined if a receptacle -2- is housing the required base product or not, and if it is in a liquid state or not.

Figure 8:
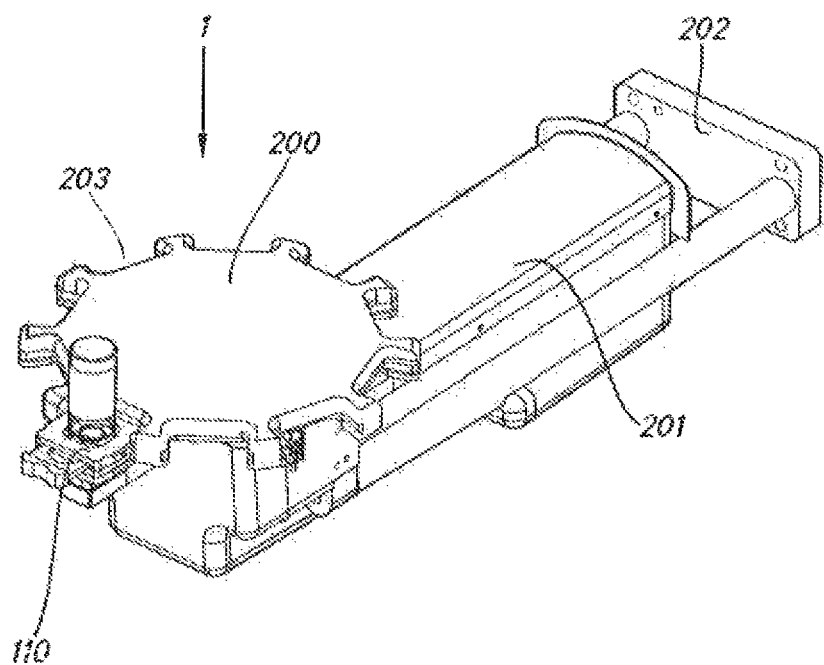
FIG. 8 shows an example of a starting products area according to the present invention.

FIG. 8 shows an exemplary starting products area -1- which comprises a rotatable unit -200- with several slots -203- around its perimeter so that vial holding devices -110- can be disposed therein. The rotation of the unit -200- allows the translation between an active position (where a robotic arm can actuate and a passive position (e.g. for intermediate storage of vials).

In a preferred embodiment the rotatable unit -200- comprises one active position for each of the robotic arms of the machine so that one arm can, for example, be designated for vial actuation. The arm designated for vial actuation can move the vial to a filling reconstituting area and perform the actions required on the vial (such as inserting a needle through the vial, agitating a vial, etc.) and the arm designated for syringe actuation can, simultaneously, take a syringe, remove its cap, weight the syringe. After this simultaneous process occurs the vial is disposed in the rotatable unit -200-, which is located in the first active position (which is the active position for the robotic arm designated for vial actuation), then the unit -200- rotates from the first active position to the second active position (which is the active position for the robotic arm designated for syringe actuation) where the second robotic arm inserts the needle through the vial and withdraws/inserts liquid. As can be seen, in this embodiment the rotatable unit -200- interrelated two of the arms thereby allowing simultaneoueness and, consequently, a faster process.

Figure 9:
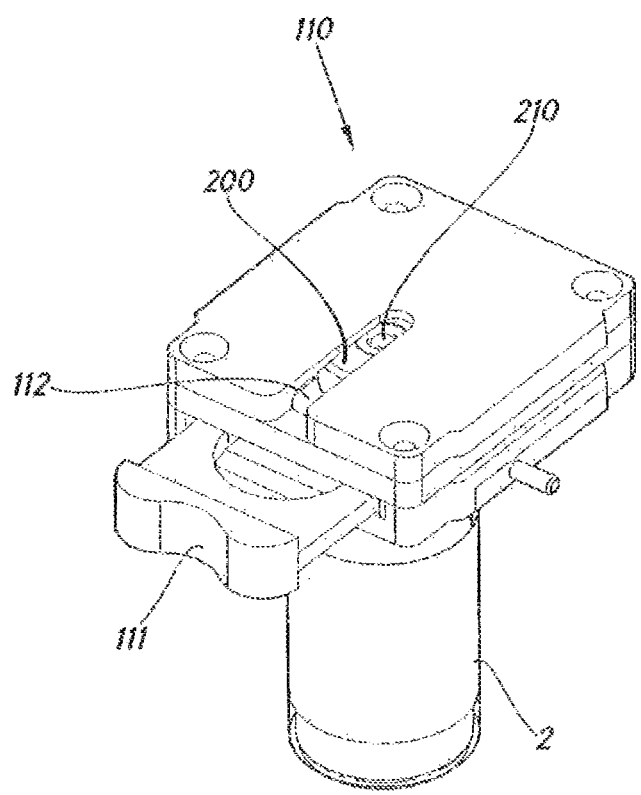
FIG. 9 shows a tool for engagement/centering of vials.

FIG. 9 shows an exemplary vial holding device -110-. This vial holding device allows the use of different types and sizes of vials maintaining the same grip and avoiding the need for different programming on the robotic arm for each size/type of vial.

Surprisingly, the use of such a holding device -110- allows the actuation on a vial directly from the arm. For example, the grip can be more accurate and firm allowing the arm, for example, to agitate a vial without the need for contact with the glass part of the vial. Prior are robotic arms comprises a metallic clamp and hold the vial on its glass part thereby adding a risk of metal-to-glass contact and making it extremely unsafe to perform an agitation procedure. The prior art devices solve this issue by complex programming and measurement of the forces involved in the gripping of the vial and the initial detection of the vials shape/size but, anyway, for security reasons it is not recommendable to perform an agitation procedure by the robotic arm, therefore, an "agitation station" has to be added to the machine. The present invention does not requires this complex preplanning or an agitation station since the clamp of the robotic arm always grips holding devices -110- with, substantially, the same dimensions and agitation can be performed directly in a safer manner by the robotic arm.

It is to be noted that the agitation procedure is simply an example of the operations that can be performed by the robotic arm designated for vials. Other operations include, but not limited to, function of the vial to a fixed needle, weighing of the vial, etc.

The vial holding device -110- further comprises a groove -112-, a release tab -111- and elastic means to maintain the vial in its position at all times.

Also, this holding device allows the centering of the vial's head -200- so that vials of every size maintain, at least, one common coordinate of where the elastomeric -210- portion of the vial is located. This allows other operations, such as, pushing the vial against a needle for the vials filling, for example, by a peristaltic pump (not shown).

The holding device further comprises elastic means which, together with an endwall, maintain the vial fixed at all times.

Figure 10:
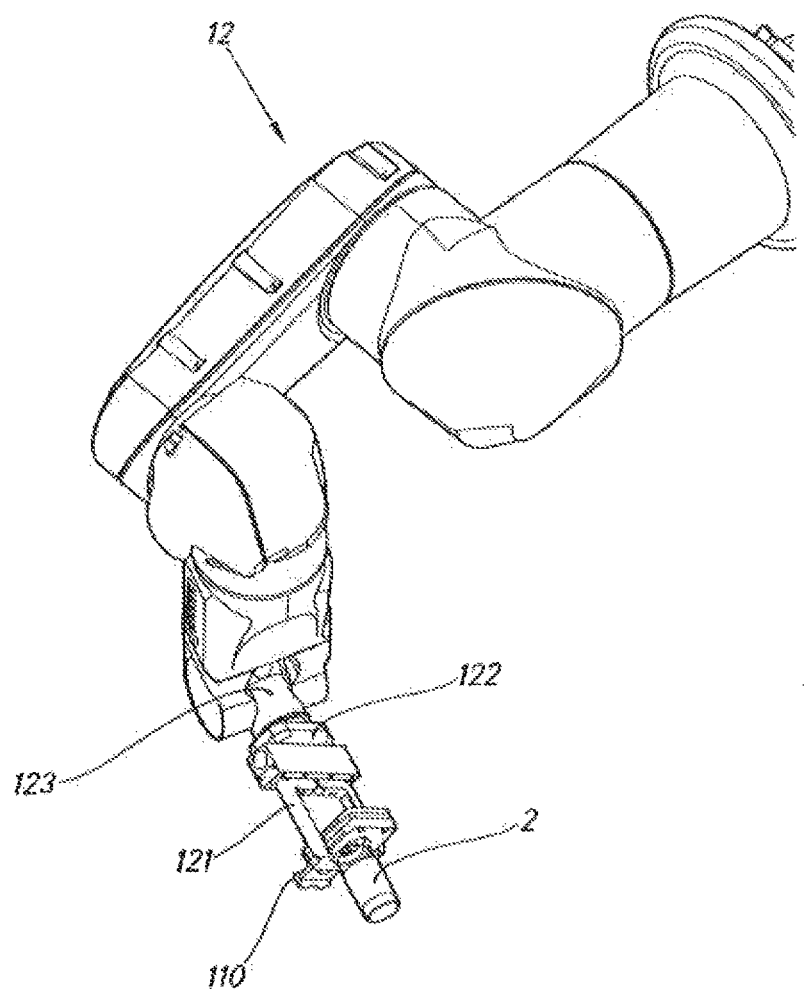
FIG. 10 shows the tool of FIG. 8 coupled to a robotic arm.

FIG. 10 shows a holding device being hold by a first robotic arm -12-. This figure shows that the robotic arm further comprises a clamp -121- for gripping the holding device -110- and, subsequently, a vial -2- and by the actuation of a first articulation -122- and a second articulation -123- actions, such as agitating, or filling of a vial can be performed, as explained above.

The agitation of a vial is a periodic movement, preferably a pendular movement using one articulation of the robotic arm, with a frequency of at least 1 Hz in order to guarantee that a lyophilized product disposed on the receptacle is completely dissolved in a fluid.

Figure 11:
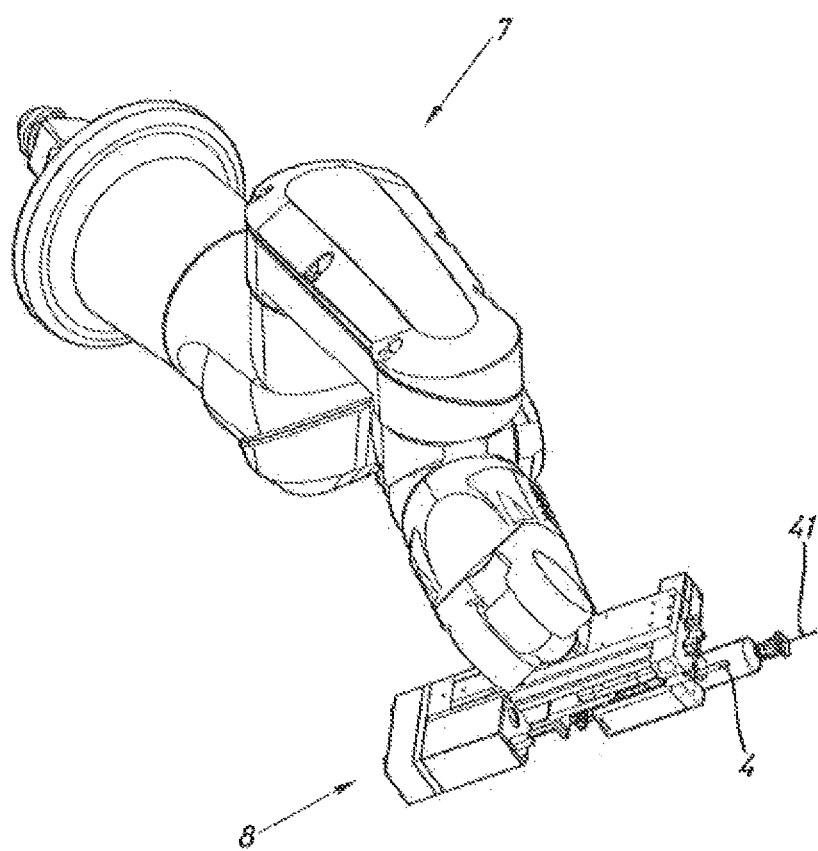
FIG. 11 shows another tool attached to a robotic arm.

FIG. 11 shows an embodiment wherein a second robotic arm -7- comprises an actuating device -8- for the conveying and/or actuating on a syringe -4- comprising a needle -41-. Said actuating device can move the plunger of the syringe for injecting fluid from a receptacle or retrieving fluid from it.

Figure 12:
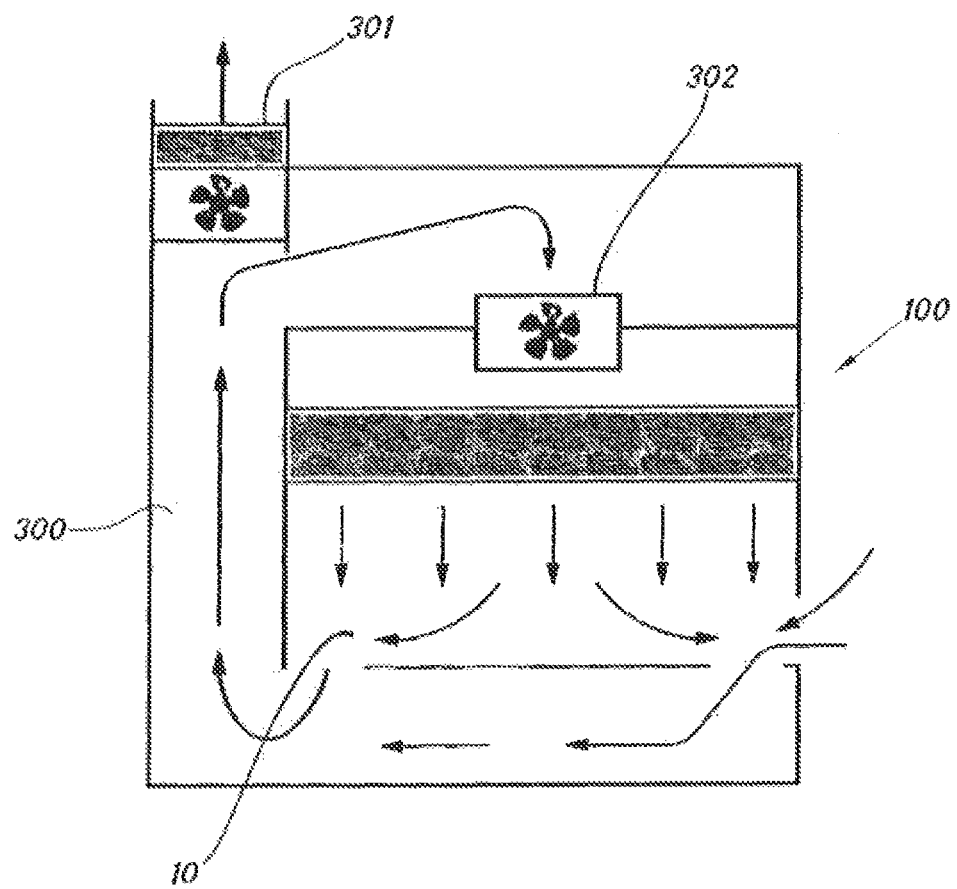
FIG. 12 shows the airflow in a machine according to the present invention.

FIG. 12 shows the airflow on the chamber -10- that will be helpful for explaining the cleaning principle of the machine.

Machines for automatic preparation of intravenous medications have to comply with cleanroom standards such as, for example, ISO 5, Therefore HEPA (High-Efficiency Particulate Arresting) or ULPA (Ultra-Low Penetration Air) filters must be disposed to clean the air on top of the preparation area, so that the input air is sterile.

As shown in FIG. 12, the airflow of an embodiment of the present invention is a laminar airflow in the chamber -10- said airflow is forced down and follows a path -300- where the air is ejected through the conduct -301- and most of the airflow is recovered. Such a configuration requires that a purification or cleaning filter is located below the chamber -10- so that most of the chemical or microbiological contamination that arise in the preparation chamber are retained before recirculation or ejection of the air from the machine.

Prior art devices comprise bacterial cleaning means that further include an UV lamp but such cleaning means do not perform a chemical sweep.

This chemical sweep using water spraying is performed by an embodiment of a machine according to the present invention by the spraying of water and the movement of the robotic arms thereby allowing the water to flow throughout the machine. In one embodiment the robots move to a "cleaning position" where the robots are away from places susceptible to chemical spills so that water or other cleaning fluids can reach those places. In other embodiments the robots move throughout the machine in order to guarantee that they get in touch with the water, therefore cleaning themselves.

Given that the filters are delicate and cannot get in touch with water contaminated by chemical substances swept by the cleaning means, drainage means are disposed to evacuate from the chamber -10- at least part of the fluid introduces by the cleaning means, avoiding that the water or cleaning solution wets the filters, said drainage means comprising at least one drainage hole -20- disposed in the bottom part of the chamber -10- and at least one drainage surface -21- in said bottom part of the chamber -10- to guide the fluid to the drainage hole -2-.

The invention claimed is:

1. A machine for automatic preparation of an intravenous medication in a chamber of the machine, comprising:
    (a) a starting products area comprising at least one receptacle with a base product;
    (b) a transfer tools area comprising at least one transfer tool;
    (c) a prepared products area comprising at least one container to house the prepared medication;
    (d) a first robotic arm configured to transport the at least one receptacle among the starting products area, the transfer tools area, and the prepared products area; and
    (e) a second robotic arm configured to transport the at least one transfer tool among the starting products area, the transfer tools area, and the prepared products area;
    wherein the starting products area, the transfer tools area, the prepared products area, the first robotic arm and the second robotic arm are disposed in the chamber.

2. The machine of claim 1, wherein the at least one receptacle further comprises a head with an elastomeric portion, a neck and a body.

3. The machine of claim 1, further comprising a holding device, wherein the holding device comprises an elastic means configured to hold the at least one receptacle from its neck.

4. The machine of claim 3, wherein the holding device further comprises a groove that matches the elastomeric portion of the at least one receptacle.

5. The machine of claim 1, wherein the first robotic arm is further configured to agitate the at least one receptacle.

6. The machine of claim 5, wherein the agitation is a periodic movement with a frequency of at least 1 Hz.

7. The machine of claim 1 wherein the second robotic arm comprises a plunger actuator.

8. The machine of claim 1, wherein the first robotic arm comprises a holding means.

9. The machine of claim 1,
    wherein the first robotic arm comprises a first holding means;
    wherein the second robotic arm comprises a second holding means, wherein
    the second holding means comprises a plunger actuator.

10. The machine of claim 9, wherein the at least one receptacle comprises a head with an elastomeric portion, a neck and a body.

11. The machine of claim 10, wherein the first robotic arm further comprises a holding device, wherein the holding device comprises an elastic means configured to hold the at least one receptacle from its neck.

12. The machine of claim 11, wherein the holding device further comprises a groove that matches the elastomeric portion of the at least one receptacle.

13. The machine of claim 9, wherein the first robotic arm is further configured to agitate the at least one receptacle.

14. The machine of claim 13, wherein the agitation is a periodic movement with a frequency of at least 1 Hz.

15. The machine of claim 1, further comprising a cleaning means for cleaning at least part of the chamber, the cleaning means comprising at least one hole through which a sprayed liquid or a fluid in the form of a jet is introduced into one or more certain areas of the chamber or in said chamber in its entirety.

16. The machine of claim 15, further comprising a drainage means to evacuate from the chamber at least part of the fluid introduced by the cleaning means, the drainage means comprising at least one drainage hole disposed in the bottom part of the chamber and at least one drainage surface in the bottom part of the chamber to guide the fluid to the drainage hole.

17. The machine of claim 15, further comprising a drying means to dry the walls that delimit the chamber and the elements present in the chamber of the fluid introduced by the cleaning means, the drying means comprising an inlet access in a top part of the chamber, at least one flow router on the chamber to force the flow inside the chamber through the inlet access and until it is evacuated from the chamber through a bottom part of the chamber, and an outlet access disposed in the bottom part of the chamber through which the flow is forced out of the chamber.

18. The machine of claim 15, wherein the first robotic arm and the second robotic arm are each further configured to move to a predetermined position during cleaning.

19. The machine of claim 15, wherein the first robotic arm and the second robotic arm are further configured to move while cleaning for ensuring that they get in touch with the fluid.

* * * * *